United States Patent [19]

Zöld

[11] 4,175,662
[45] Nov. 27, 1979

[54] METHOD AND DEVICE FOR SORTING PARTICLES SUSPENDED IN AN ELECTROLYTE

[76] Inventor: Tibor Zöld, Schmale Strasse 19, 44 Münster, Fed. Rep. of Germany

[21] Appl. No.: 888,900

[22] Filed: Mar. 22, 1978

[30] Foreign Application Priority Data

Apr. 12, 1977 [DE] Fed. Rep. of Germany ....... 2716095

[51] Int. Cl.² .................... B07C 5/04; B07C 5/342
[52] U.S. Cl. .................................. 209/552; 209/606; 209/643; 209/644; 209/906; 209/933; 209/934; 406/47; 406/50; 406/197
[58] Field of Search .................... 209/3, 552, 563, 564, 209/576, 577, 579, 586, 606, 638, 639, 643, 644, 932, 934, 906; 302/66

[56] References Cited

U.S. PATENT DOCUMENTS

| | | | |
|---|---|---|---|
| 3,514,217 | 5/1970 | Reiss | 302/66 X |
| 3,560,754 | 2/1971 | Kamentsky | 209/906 X |
| 3,791,517 | 2/1974 | Friedman | 209/579 |
| 3,826,364 | 7/1974 | Bonner et al. | 209/638 X |
| 3,827,555 | 8/1974 | Kamentsky et al. | 209/579 X |
| 4,009,782 | 3/1977 | Grimshaw | 209/606 X |

*Primary Examiner*—Joseph J. Rolla

[57] ABSTRACT

The invention discloses a method and apparatus which allows the sorting of particles or cells in accordance with their physical and/or chemical properties such as size, DNA and/or protein content. The present invention is furthermore characterized in that the device of the invention is combined with at least one analyzer system which is sensitive to at least one of the above or other properties and which converts the well defined property into an electrical impulse and, after analysis, directs the flow of particles into the sorter where the particles are to be sorted according to their analyzed properties in such a manner that an electrolysis gas impulse can be produced between the pairs of platinum control electrodes in each side channel of the sorter by supplying a short current impulse to said pair of electrodes; clearly, the production of such a gas impulse results in a reduction of the suction effect in this channel applied by an external suction pump and a deflection of the suspension stream which accordingly flows in the middle of the entrance channel into the other side channel lying opposite to said side channel in which the gas impulse is produced. The triggering of the impulse is provided by electronic equipment attached to the analyzing part of the device.

38 Claims, 7 Drawing Figures

METHOD AND DEVICE FOR SORTING PARTICLES SUSPENDED IN AN ELECTROLYTE

This invention is concerned with a method and device for the control of motion and especially for the sorting of particles of an electrolytic suspension, where the input flow path can be split up into several output channels leading to respective receptacles. This invention furthermore, is concerned with a sorting device in which by the production of gas particles or cells can be sorted out in accordance with their physical and/or chemical properties such as, particle (cell) size, DNA and/or content.

Such a method and device are especially useful in cytology for the sorting of cells such as tumour and/or blood cells or in the study of micro-organisms.

Such a method and such a device are already known, see for instance: "Electronic Separation of Biological Cells by Volume" by M. J. Fulwyler in Science vol. 150, pp. 910–911, November (1965) or "High-Speed Cell Analysis and Sorting with Flow Systems: Biological Applications and New Approaches" in IEEE Trans. on Nuclear Science, NS-21, pp. 714–720 (1973). The operation of the known method and device is as follows:

In a flow chamber with a capillary exit of very small diameter a very thin (cca. 25 micron diameter) stream of the suspension is produced. A piezoelectric resonator breaks this stream up into small droplets by producing very large ultrasound waves in the suspension stream. Before the breaking-up the particles (cells) pass through the focused beam of an argon laser. The fluorescent light and the scattered light are converted into electrical impulses through the use of photomultipliers and analysed by equipment attached to the sorter.

When a particle (cell) is to be sorted out in that known device the suspension stream is charged by suitable equipment shortly before the break-off of the droplet containing the mentioned particle after detecting the desired quantity by the attached optico-electronic system. Droplets not containing any of the cells to be sorted will not be charged. Then, the droplet stream additionally flows through a very strong electrostatic field of several thousand volts per centimeter, where it will break up into two or more divisional streams depending on the polarity and charge of the charged droplets, and the various divided streams are collected in different small containers. In the known device about $5 \times 10^4$ cells are produced per second. As was reported by van Dilla e.a. two or more different kinds of cells can be separated from a mixture at a rate of about 200 cells/sec and with a purity of about 90%. The Fulwyler method described above is relatively sensitive to the size of cells or polystyrene beads and needs a strong light source such as a laser to produce scattered light strong enough for the relatively weak optical system.

Therefore, it is one object of the invention to provide a method and a device for controlling the flow of an electrolyte in closed channels of capillary size in order to make possible the sorting of at least one but rather two kinds of particles (cells) from a mixture; as a result of the closed arrangement of the flow system the device according to the invention is more rugged than the Fulwyler device described above.

In accordance with the invention this problem is solved in such a manner that the electrolyte flowing in a channel can be split into at least two side channels and that the thin suspension stream can be deflected completely into at least one of the side channels from the entrance channel or middle channel by producing a sudden and short electrolysis gas impulse in that side channel lying opposite to the side channel in which the suspension stream is to be deflected. This method of sorting is based on the direct changing of the electrolyte flow path while the suspended particles are deflected only indirectly by this change of the electrolyte flow.

In accordance with the invention the above problem is solved by such a device which allows the sorting of particles or cells in accordance with their physical and/or chemical properties such as size, DNA and/or protein content. The present invention is furthermore characterised in that the device of the invention is combined with at least one analyser system which is sensitive to at least one of the above or other properties and which converts the well defined property into an electrical impulse and, after analysis, directs the flow of particles into the sorter where the particles are to be sorted according to their analysed properties in such a manner that an electrolysis gas impulse can be produced between the pairs of platinum control electrodes in each side channel of the sorter by supplying a short current impulse to said pair of electrodes; clearly, the production of such a gas impulse results in a reduction of the suction effect in this channel applied by an external suction pump means and a deflection of the suspension stream which accordingly flows in the middle of the entrance channel into the other side channel lying opposite to said side channel in which the gas impulse is produced. The triggering of the impulse is provided by electronic equipment attached to the analysing part of the device. In this manner a particle mixture can be divided into a least two groups each of which can be collected in a separate container at the exit of the capillary side channels.

It is one advantage of the present invention that the controlling of the suspension stream takes place in closed channels of capillary size and that the particles need not flow through a very strong electrostatic field. Thus, this device is rather rugged and less expensive than the known device described above.

It is a very important feature of the present invention that the amount of gas produced between one pair of control electrodes in one side channel should be so large that the flow of the electrolyte in this respective channel comes to a stop whereby the electrolyte continues to flow in the other side channel—in the case of a sorter system with only two side channels—. When a gas impulse corresponding to a definite particle is properly triggered, i.e. just before this particle reaches the control electrodes, this particle will be directed into the other side channel i.e. into the corresponding container. The deflection of a particle into the first side channel can be achieved the production of a gas impulse in the second side channel in the same manner as described for the first side channel.

From the above description follows that by properly triggering the present device any particle is deflected opposite to the channel where the electric field and thus the gas is produced. The cells do not flow through a high electric field in this device, in contradistinction to the known device described above.

According to a preferred embodiment of the invention a middle channel is provided with relatively large cross-section, or more preferably, the channel should be rather wider than deep. In this middle channel there flows a rather thin suspension stream surrounded by a laminar stream of pure electrolyte. In the quiescent state the suspension stream flows right at the center of the middle channel. The middle channel at its downstream end splits up into at least two but rather three or more side channels symmetrically arranged with respect to the center of the middle channel, obtaining in this manner a system with two, three, or more side channels in which one, two, or more kinds of particles can be separated, respectively, in accordance with their properties, analysed in the analysing system located at the upstream end of the sorter and transformed into respective electrical impulses used to trigger the control electrode pairs at appropriate times, i.e. just before the particle corresponding to a certain trigger impulse reaches the selected pair of control electrodes. Such a system operates in the following manner for a sorter comprising as an example two side channels only: When a short impulse of gas is produced in one of the side channels the suspension stream is deflected towards the other side channel as described above, provided this gas impulse is properly triggered, i.e., at the correct time. The particle corresponding to the trigger impulse and moving in the suspension stream is deflected into that side channel in which the gas impulse was not produced. The same effect can be achieved with electrode pairs located for example on the inner surface walls of the middle channel. In this case, gas produced at one side of the middle channel will result in a deflection of the suspension stream away from the electrodes and thus, into the side channel remote from the side at which the gas impulse was produced. While two possibilities exist for the location of the control electrode pairs it should be noted that the embodiment with control electrode pairs within the side channels is more effective because here the electrodes of a pair can be provided in parallel to each other on opposite sides of the inner surface of the side channels. By this arrangement a more powerful gas production results.

In accordance with the invention a plurality of side channels can be provided at the end of the middle channel and by properly triggering the gas impulses the suspension stream can be deflected successively into any of these side channels, thus providing a means to sort particles of more than one or two kinds at one and the same flow-through of the particle mixture. According to a further embodiment of the invention the middle channel continues into a narrower middle exit channel into which the suspension stream continues to flow in its quiescent state. With this arrangement it is possible to connect a plurality of such channel elements or stages in series by connecting the middle exit channel of the last stage with the middle channel of the following next stage. In this case the narrow middle exit channel can be used for the same functions as the analysing system at the entrance of the sorter, It may, however, be necessary to provide two additional entrance side streams at the interface between the adjacing channel stages which flow laminar to the suspension stream in order to keep the electrolyte and hence the particle velocity constant through the whole sorter system.

If the suspension stream is not deflected in the first channel stage it can be deflected in the next channel stage providing in this manner a further possibility to distribute the particle mixture into the desired plurality of groups with different characteristics.

In accordance with one embodiment of the invention the particles flow from the analyser portion through the middle channel which ends in two side channels which are perpendicular to the middle channel. In the quiescent state the electrolyte and therefore also the particle are equally split between the two side channels. In each of the side channels a pair of control electrodes is located preferably at the inner side walls of the side channels in such a manner that the electrodes of each pair are aligned in parallel to each other. When a particle to be sorted out from the mixture is programmed to enter into the left side channel an appropriate amount of gas is produced by supplying the electrodes in the right side channel with a trigger impulse at the right time to block this side channel for the passing of the respective particle. By this blocking action only in the left side channel suction will be exercised on the electrolyte sucking in this manner the particle into the left channel. All the other particles which do not arrive at the same time at the electrodes in the right channel will enter into the right side channel due to the production of gas impulses in the left side channel. Due to its shape this embodiment is called T-sorter.

In an improved embodiment of the T-sorter the suspension enters into the middle channel in a very thin hydro-dynamically focused stream. In this case the velocity of all particles within the stream is about the same. Thus, the proper triggering of the gas production relative to arriving particles is facilitated as the flow velocity is strongly dependent on the position of the particle relative to the middle axis of the channel.

In a hydrodynamically non focused version of the T-sorter about 90% of the particles (latex beads) were found in the proper channel for about 200 cells/sec., while the result was about 80% for similarly conducted experiments and 400 to 500 cells/sec.

An embodiment similar to the T-sorter is the so-called Y-sorter which can, however, operate only in the hydro-dynamically focused form. In this device two side streams enter laminarly preferably on both sides of the suspension stream at the upstream end of the middle channel in parallel alignment to the very thin suspension stream.

The two side channels in this version are provided with equal acute angles relative to the axis of the middle channel where the thin suspension stream flows. The gas producing electrode pairs can be located either in the side channels in the same manner as in the T-sorter or at the inner wall of the middle channel slightly before the branching into the side channels. In any case, the thin suspension stream can be deflected into either of the side channels by the production of gas impulses either in the opposite side channel or at the electrode pair located on the opposite side of the middle channel. It follows from its advantageous geometry that the sorting capability of the Y-sorter is higher than that of the T-sorter.

In another embodiment of the invention the middle channel is branched into three narrower channels, the middle exit channel and the two side channels, symmetrically arranged to the middle exit channel, such that the suspension stream in the quiescent state flows in the substantially straight middle exit channel. Either only the two side channels or the two side channels and the middle exit channel have a pair of gas producing electrodes. In the first case the side channels should be several times wider than the middle exit channel in order to achieve an appropriate deflection of the suspension stream. With this model two different kinds of particle groups can be sorted by the two deflection paths of the suspension stream. This device will be called "Ψ-sorter". Clearly such a channel element or stage can be connected in series, in such a manner that the middle exit channel is provided at its downstream end with two additional laminar side streams forming in this manner another middle channel which can be branched into another triplet of channels as was the case in the first stage of the device. With such a multiple system a very large number of particle groups with different characteristics can be sorted out from the mixture by one and the same flow of the mixture.

Preferably, the gas producing electrodes are made of platinum material.

As particle analysing section or "sensor" some of the known devices can be used. One of these is the so-called channel counter described in copending U.S. application Ser. No. 888,899 filed Mar. 22, 1978 having specific conductivity different from that of the electrolyte in which they are suspended. Such a channel counter consists of a first counter electrode, an orifice, and a second counter electrode, the suspension flowing through the small orifice and the first and second counter electrodes are provided at the upstream and downstream sides of the orifice, respectively. In this known device the passage of a particle through the orifice corresponds to a resistance impulse dependent on the size of the particle and this resistance impulse is converted into a current and/or voltage impulse which is further analyzed in the attached electronical system. This channel counter is characterised in that the orifice is located between an entrance—, and an exit-channel, and that the counter electrodes are located either outside the channel system in small containers which are connected to said channels through flexible tubes or in said channels adjacent the orifice.

As another sensor the optical axis of the microscope of a known impulse cyto-photometer (I.C.P.) can be located additionally at the very vicinity of the orifice of the channel counter or simply across the hydrodynamically focused suspension stream at a definite angle. Thus, in addition to the measurement of the particle (cell) volume other quantities of the particles such as DNA and/or protein content can also be analysed and sorted in accordance with the amount of any of the quantities mentioned above and presumably with other quantities, too.

Furthermore, as sensor a laser system can also be combined with the device of the invention when the focused suspension crosses the focused light of a laser. In such a combination the measuring chamber should be constructed such that the particles can interact with the laser beam without great loss in the fluorescence or the scattered laser light. In some cases the sorter can be combined with a Crossland-Taylor I.C.P. system well known in the literature. In accordance with the principles of the invention there is an additional field of use for the controlling of the electrolyte flow by electrolytic gas production in order to reduce the large distance and irregular sequence of particles flowing in a channel or very small cross-section. Such a device consists of a main channel for the suspension from which at least one side channel branches out substantially perpendicular and provided with control electrodes. By the control of the electrolyte output through the side channels which reduces the electrolyte content of the suspension, the spacing between two particles can be controlled during the time in which any of the particles are remote from the side channel. An electronic circuit controls the gas production of the electrodes and receives the control impulses from a sensor, such as a channel counter, in such a manner that the spacing between two particles can be reduced to a desirable extent by letting out the appropriate amount of electrolyte through the side channels. In the programming of such a system or device care must be taken that neither of the particles can enter the side channels because such a particle would be lost. This is achieved by closing the side channels with the aid of the gas production at the control electrodes during the particles pass the side channel entrance.

Such a spacing-compressor allows to speed up the operation of particle (cell) analysis and sorting.

These and other features and objects of the present invention will become more apparent upon a perusal of the following description taken in conjunction with the accompanying drawings wherein.

Figure 1:
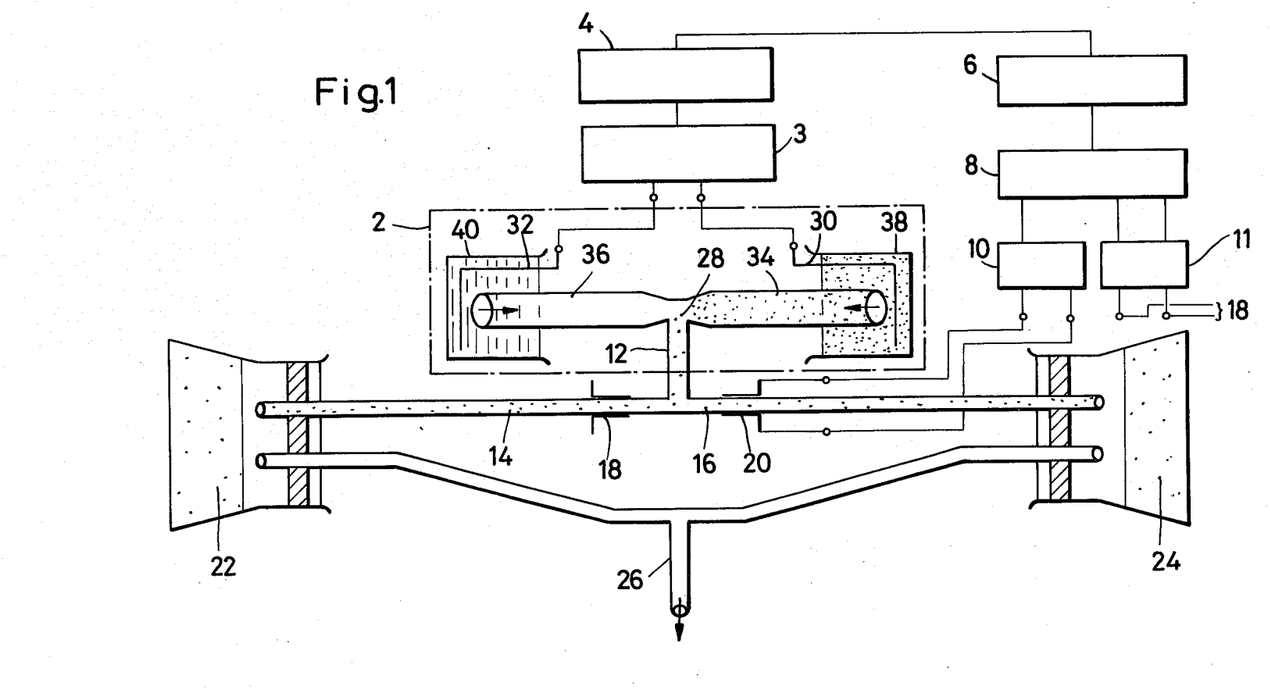
FIG. 1 represents a schematic view of a first embodiment of the invention, the so-called T-sorter, with a simple version of the channel counter as sensor combined with the necessary electronic circuity.

FIG. 1 shows a first embodiment of the invention, the so-called T-sorter, and a channel counter as volume sensor as lines 21 and 22 have been rewritten as the above referred to co-pending application. A capillary exit channel 12 of the channel counter 2 which serves as a volume sensor for the particles suspended in an electrolyte, branches at its downstream end into two side channels 14 and 16 of the same cross-section and length transversely to the axis of the exit channel 12. By flexible tubes the side channels are connected to the containers 22 and 24, respectively, which are under low vacuum, to exercise a suction effect on the contents of the side channels via tube 26 which in turn is connected to a suction pump (not shown). Under the suction operation of the pump suspension electrolyte and pure electrolyte flow from containers 38 and 40, respectively, into the counter 2 where they mix and continue to flow through the exit channel 12 and equally divided through the side channels 14, 16 and finally into the containers 22 and 24, respectively. In each of the side channels 14 and 16 a pair of control electrodes 18, 20 is located preferably on the surface of the channel wall. The control electrodes 18, 20 produce controlling gas impulses at the proper time determined by the electronic circuit, which transmits a voltage impulse to the selected control electrode pair for each single control action.

The channel counter 2 as described in the above referred to co-pending is related to the well known Coulter counter, yet it shows many new features and properties which make it distinct from the known Coulter-counter. These properties are on one hand, cf. FIG. 1, that the suspension flowing from container 38 through the entrance channel 34 and the orifice 28 continues to flow in the relatively narrow capillary exit channel 12 after mixing with pure electrolyte from container 40 and another entrance channel 36, thus making possible the lining-up of the particles for further analysis or sorting. A further characteristic of the channel counter is that both of the counter electrodes 30 and 32 are located in relatively large containers 38 and 40, respectively, therefore the counter electrodes can be of arbitrarily large size and the gas, produced at these electrodes by electrolysis of the electrolyte can freely leave the counter electrodes without disturbing the operation of the counter and without producing large background noise. From this arrangement follows that a particle flowing from container 38 and passing through the relatively narrow orifice 28 produces a change in the electrical resistance between the counter electrodes 30 and 32. This resistance impulse corresponds to a current and/or voltage impulse which will be further analysed by the electrical circuit connected to the control electrodes 30 and 32. According to FIG. 1 this circuit comprises an emitter-follower 3 for impedance transformation, a band-pass filter 4 to reduce the feedback effect from the control electrodes 18 and 20 on the sensitive electrical counter circuit, an amplifier 6, a logic unit 8 for the analysis of the counter impulses and two pulse formers 10 and 11 to energize the control electrodes 20 and 18, respectively at the proper time and with the proper impulse determined by the logic unit 8.

The operation of the T-sorter is as follows: Under the suction effect of the pump (not shown) connected to the tube 26 suspension and pure electrolyte flow from containers 38 and 40 through the entrance channels 34 and 36, respectively, towards the orifice 28 into the exit channel 12 and then through the side channels 14 and 16 into the containers 22 and 24, respectively. The side channels 14 and 16 are substantially identical such that the passing electrolyte and the number of particles is the same within a few percent in both channels. Now, the probability to direct a particle into the side channel 14 is very high when the following requirements are fullfilled: The cell or the particle flows through the orifice 28 and produces an electric impulse in the electrical circuit by which the impulse former 10 is triggered from the logic unit 8 and produces such a large current impulse through the control electrode pair 20 that the gas production of the electrodes 20 stops the flow of electrolyte in side channel 16 at the moment the particle (cell) has just arrived the branch point between the exit channel and the two side channels. The logic unit 8 determines the moment when the gas production by the pair of control electrodes 20 should begin. Typical values found for the current amplitude, the pulse width and the delay between the counter impulse and control impulse are 250 mA, 400 microseconds and 150 microseconds, respectively. The current impulse can be calculated approximately by the data given for electrolysis, taking into account that for stopping the flow of electrolyte in a channel the same amount of gas is necessary as the amount of water that would flow in the channel per unit time in the quiescent state. Typical results with such a T-sorter and small latex beads as particles were about 90% sorting of particles for 200 beads/sec and about 80% sorting for 400-500 beads/sec flowing through the sorter. The type of particles (cells) sorted in such a manner are collected in a bottle type container 22 while the remaining particles are collected in container 24. When the impulse-former 11 is triggered by the logic-unit then the particle will enter with high probability into the side channel 16 and will be collected in bottle 24 and in this manner a type of particles with well determined properties can be sorted into either of the containers 22 or 24.

Figure 2:
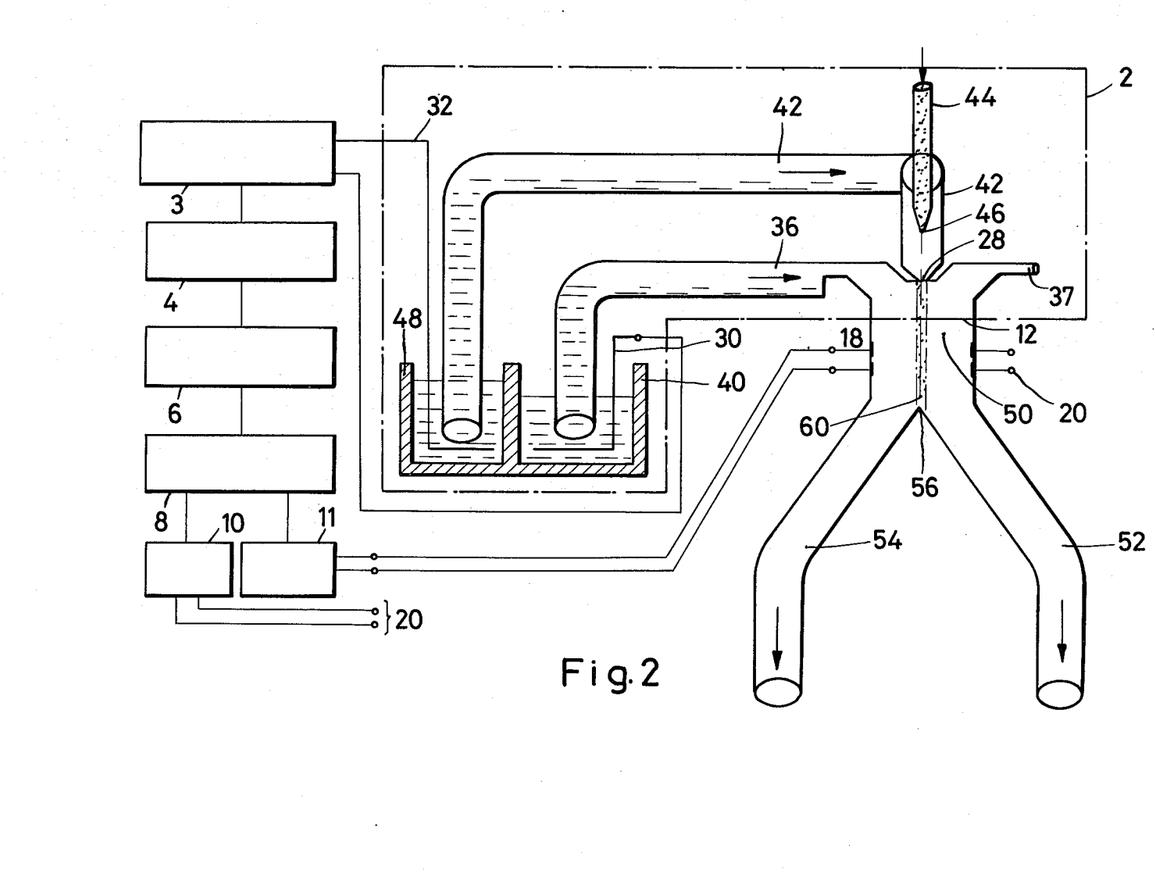
FIG. 2 is a schematic view of a second embodiment of the invention, the so-called Y-sorter, also with the necessary electronic circuits comprising as sensor a hydrodynamically focused channel counter.

FIG. 2 shows a second embodiment of the invention, the so-called Y-sorter. The electronic system for this version is the same as in FIG. 1. However, the so-called hydrodynamically focused version of the channel counter is used as a volume sensor also described in the above referred to co-pending application. In this version, as can be seen in FIG. 2, the suspension is injected into the counter through a very thin capillary tube 44 which ends in a nozzle 46 and is located substantially coaxially inside the entrance channel 42; the pure electrolyte flowing in the entrance channel 42 focuses the suspension into a very thin stream at the upstream side of the orifice 28 concentrically with the orifice from where the suspension further flows into the exit channel or middle channel 50 of the sorter device. Adjacent the orifice 28 pure electrolyte enters laminarly at both sides of the suspension stream 60 through the side entrance channels 36 and 37 to keep the suspension stream 60 at the center of the middle channel 50 and to direct the suspension and thus, the particles, right against the tip 56 of the branching of the middle channel 50 into the two side channels 52 and 54. The pairs 18 and 20 of control electrodes are provided at a small distance before the branching of the middle channel 50 on the inner side walls of the middle channel. Alternatively, the pairs of control electrodes can also be provided in the side channels 52 and 54 in the manner shown in FIG. 1. The deflection of the suspension stream 60 into one side channel, say into channel 52, is achieved by producing a sufficiently large amount of gas by the control electrodes 18; the control electrodes 20 would, clearly, produce the deflection of the suspension stream into the side channel 54. It is an advantage of this embodiment that the deflection of the very thin suspension stream 60 is simpler and faster than in the T-sorter and as a result faster operation can be achieved with the Y-sorter than with the T-sorter.

Figure 3:
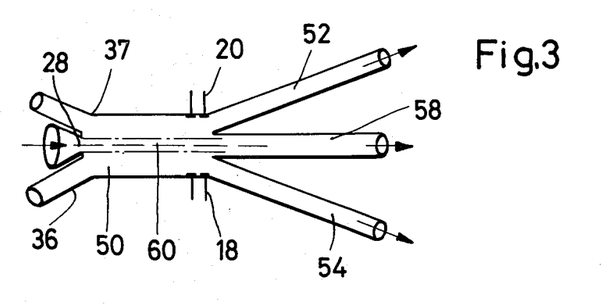
FIG. 3 is a schematic view of a third embodiment of the invention, i.e., the principal part or channel system of the so-called Ψ-sorter which can easily replace the channel system of the Y-sorter in the arrangement of FIG. 2.
Figure 4:
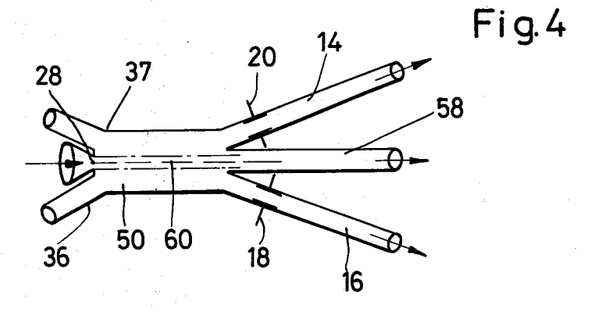
FIG. 4 and FIG. 5 are schematic views of two modifications of the Ψ-sorter with altered arrangement of the gas producing control electrodes.
Figure 5:
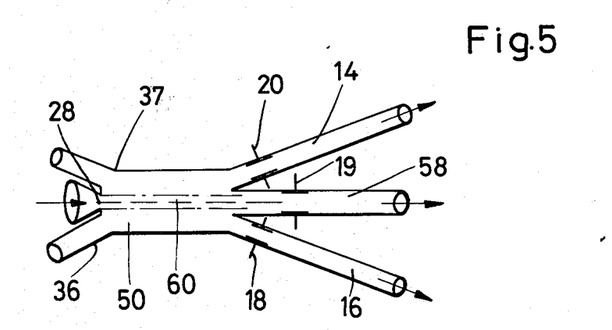
Figure 6:
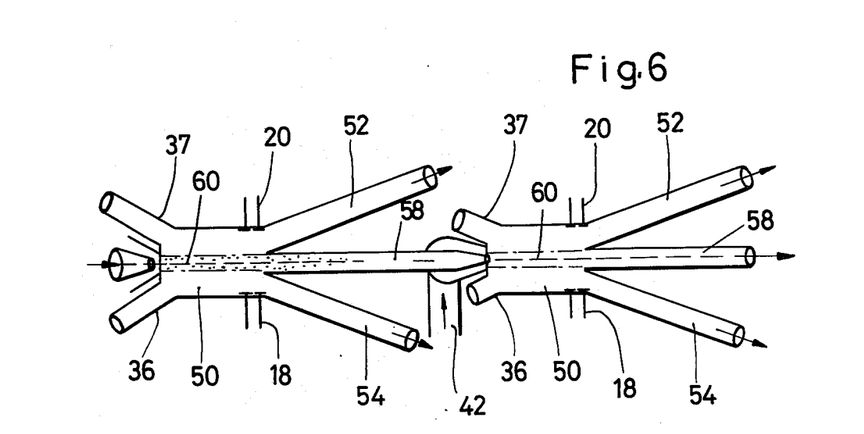
FIG. 6 is a schematic view of a series connection of two Ψ-sorters according to FIG. 3.

FIGS. 3, 4 and 5 show the so-called Ψ-sorter with three possible modifications of the pairs of control electrodes. It is an advantage of this sorter that two different kinds of particles can be sorted by the same flow-through of a mixture because the two particle groups can flow out through the side channels 52 and 54 (or 14 and 16) respectively, while the remaining part of the mixture flows through the middle exit channel 58 which is colinear to the middle channel 50. In the quiescent state the suspension stream 60 flows through the middle exit channel 58 which allows a series connection of a plurality of such sorter elements as is shown in FIG. 6. It should be noted that the side channels should be several times wider than the middle exit channel 58 in the arrangement of the control electrodes as shown in FIGS. 3 and 4, in order to achieve sufficiently large deflection of the suspension stream into either of the side channels. This is not necessary for the embodiment shown in FIG. 5 because the control electrode pair 19 of the middle exit channel 58 provides greater deflection force on the suspension stream than in the first two embodiments.

Figure 7:
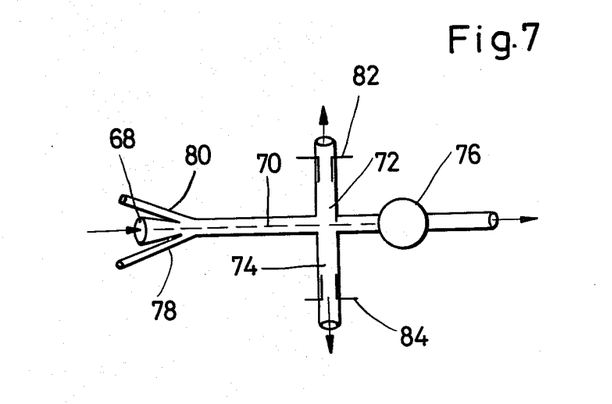
FIG. 7 is a schematic view of a particle spacing compressor device according to the invention.

FIG. 7 shows the channel arrangement of a device which in accordance with the invention is capable to reduce the interparticle spacing of particles suspended in a suspension stream in a capillary channel. The particles flow through a channel counter 68, 78 and 80 into a main channel 70 of capillary cross-section from which two side channels 72 and 74 branch out symmetrically each of which being provided with a valve-electrode pair 82 and 84, respectively. The valve-electrode pairs 82 and 84 are programmed by an electronic system (not shown) such that the amount of the electrolyte and hence the spacing between two particles in the main channel is reduced to a desired value at those intervals during which no particle passes across the entrance of the side channels. With the reduction of the interparticle spacing the operation of another analyser such as an impulse cyto-photometer 76 can be improved since the through-put of the particles through the analyzer will be somewhat increased. It should be understood that the programming of the system should be such that the suction effect exerted from the side channels should be zero when a particle passes these channels.

I claim:

1. Method to direct the flow of electrolyte and especially the motion of particles or cells in an electrolyte suspension to sort these particles or cells from a mixture into different containers according to their preselected properties, characterized in that the suspension flows in a middle channel along a preselected length of its trajectory in the form of a very thin stream and can be deflected into at least one side channel, that a pair of control electrodes is located in at least one of the side channels, which produces gas by electrolysis when being activated by an electric current impulse of sufficient amplitude, and that the production of a gas impulse in all side channels with activated control electrodes results in a deflection of the suspension stream into those side channels with inactivated or no control electrodes.

2. Method according to claim 1 characterized in that the electrolyte in the activated side channels is reduced to a negligibly small value by each gas impulse at the pair of control electrodes in the respective side channels, thus causing a valve action in these side channels.

3. Method according to claim 1 characterized in that the middle channel, which corresponds to the entrance channel of the device, has a relative large cross-section, and that the very thin suspension stream flows laminarly and hydrodynamically focused at the center of this channel surrounded by pure electrolyte.

4. Method according to claim 1 characterized in that the middle channel branches into a plurality of side channels at its down stream end, that a pair of control electrodes is located in each of said side channels, the control electrodes being programmable such that the suspension stream can be deflected into any of said side channels by the production of a gas impulse at the control electrodes of the remaining and activated side channels.

5. Method according to claim 4 characterized in that the flow of the suspension branches into two equally shaped side channels and that the flow of the suspension in one side channel is substantially reduced to zero by a relatively strong gas impulse in this side channel, whereby the suspension is directed entirely into the other side channel.

6. Method according to claim 1, characterized in that an electronic circuit provides control impulses of different amplitude and width depending of the property of the particle analysed by a sensor and that these impulses are converted into control impulses of various amplitude, width, and delay as required for the correct deflection of the suspension stream.

7. Method according to claim 6, characterized in that each control impulse activates the corresponding control electrode pair with a predetermined delay time to achieve optimal deflection of the suspension and hence of the particles.

8. Method to direct the flow of electrolyte and especially the motion of particles or cells in an electrolyts suspension to sort these particles or cells from a mixture into different containers according to their preselected properties, characterized in that the suspension flows in a middle channel along a preselected length of its trajectory in the form of a very thin stream and can be deflected into at least one side channel, that at least one pair of control electrodes is located at the downstream end of one inner side wall of the middle channel which produces gas by electrolysis when being activated by an electrical current impulse of sufficient amplitude, and that the production of a gas impulse results in a deflection of the suspension stream into one of the side channels which corresponds to the activated pair of electrodes.

9. Method according to claim 8 characterized in that at least one pair of control electrodes is provided at each of two opposite sides within the middle channel, on the upstream side adjacent a corresponding number of side channels, that by production of a gas impulse at one of the electrode pairs the suspension stream is deflected with increasing distance from the activated pair of electrodes, and that the deflection is so large that the suspension enters the side channel remote from the activated pair of control electrodes during the production of the gas impulse.

10. Method according to claim 9, characterized in that the thin suspension stream branches equally into the two side channels during the quiescent state when neither of the control electrodes are activated.

11. Method according to claim 9, characterized in that the suspension stream in the quiescent state continues to flow in a middle exit channel located at the downstream end of the middle channel between the two side channels.

12. Method according to claim 11, characterized in that the undeflected portion of the suspension stream flows into the middle channel of a succeeding channel stage for further deflection into the side channels of said succeeding channel stage.

13. A sorter device in which the particles of an electrolyte suspension are sorted according to the magnitude of physical or chemical properties such as size, DNA and/or proteine content, characterized in that a particle-sensor produces for each particle at least one sensor impulse corresponding to the particular analysed property, that the particle-sensor directs the particles one after another into a middle channel of the sorter in which the suspension flows as a very thin stream and that at least one pair of control electrodes is located either in the middle channel or in each of at least two side channels branching from the middle channel, the pair of electrodes being selectively activated by voltage impulses from an electrical control circuit connected to the sensor such, that the activation of the preselected control electrode pairs corresponds to a deflection of the particle into the corresponding side channel.

14. A sorter device according to claim 13 characterized in that the side channels branch symmetrically with an acute angle between the side channels and the axis of the middle channel.

15. A sorter device according to claim 13 characterized in that the middle channel is of large cross-section before the branching into the side channels and that side entrance channels are provided at the upstream end of the middle channel for the laminar inflow of pure electrolyte to the suspension stream.

16. A sorter device according to claim 13 characterized in that the pairs of control electrodes are located at the inner surface walls of the side channels or the middle channel.

17. A sorter device according to claim 13 characterized in that an impulse cytophotometer is used as the sensor, the output impulses of which correspond to the amount of DNA and/or protein of the analysed particles or cells, and that the cells can be sorted into different groups according to their content of these materials.

18. A sorter device according to claim 13 characterized in that one of the sorter device and an the interparticle spacing compressor device are used in combination with an impulse cytophotometer.

19. A sorter device according to claim 13 characterized in that an exit channel of the sensor device branches into a first and a second side channel of equal and small cross-sections each of which is provided with a control electrode pair, respectively, that in the quiescent state an equal rate of electrolyte flows in both side channels, that the first side channel is substantially closed for electrolyte after activation of the first pair of control electrodes by the sensor device, due to the strong gas generation at the control electrodes of this channel, whereby the suspension and the corresponding particle only flows at this instant in the second side channel, and that activation of the second control electrode pair in the second side channel produces the deflection of the particle into the first side channel.

20. A sorter device according to claim 19 characterized in that a middle exit channel is provided between the first and second side channels.

21. A sorter device according to claim 20 characterized in that the middle exit channel is provided with a pair of electrodes for the gas production.

22. Sorter device according to claim 13 characterized in that several side entrance channels branch out from the middle channel of relative large cross-section at its upstream end, that at least one control electrode pair is provided at the inner surface of the middle channel by which the suspension stream can be deflected such that the particles can be directed into either of the first or second side channels at the downstream end of the middle channel.

23. A sorter device according to claim 22 characterized in that the side channels branch from the middle channel symmetrically with an acute angle with respect to the axis of the middle channel.

24. A sorter device according to claim 22 characterized in that the pairs of control electrodes are facing each other when located in the middle channel.

25. A sorter device according to claim 22 characterized in that the pairs of control electrodes can be located either at the downstream end of the middle channel or adjacent the branching point inside the side channels; in the latter case the electrodes of each pair are either parallelly or collinearly arranged relative to each other at opposite or the same side of the side channel, respectively.

26. A sorter device according to claim 22 characterized in that the suspension stream is directed in quiescent state right against the branching point of the side channels.

27. A sorter device according to claim 22 characterized in that a middle exit channel is provided at the downstream end of the middle channel between the first and second side channel, through which the not deflected suspension stream leaves the device and that the side channels are several times wider than the middle exit channel.

28. A sorter device according to claim 27 characterized in that the middle exit channel of a first sorter element can be connected with a middle channel of a succeeding second identical sorter element.

29. A sorter device according to claim 13 characterized in that the electronic circuit and comprises a series circuit of an emitter follower, an amplifier, a logic-unit for the selection of the desired kind of particles to be sorted from the mixture, and two impulse formers.

30. A sorter device according to claim 29 characterized in that a band-pass filter is provided between the emitter follower and the amplifier in order to reduce the feedback from the control electrodes to the particle sensor when the latter contains a volume sensor of the Coulter-type.

31. A sorter device according to claim 29 characterized in that the logic-unit contains at least one discriminator for dividing the impulses from the sensor into at least two groups according to their amplitudes that the discriminator directs the smaller impulses to one pair and the larger impulses to another pair of control electrodes whereby it divides a mixture of particles into two parts according to the magnitude of the property analysed by the sensor.

32. A sorter device according to claim 29 characterized in that the logic-unit comprises at least one window-discriminator for sorting out at least one kind of particles from the particle mixture by the correct triggering of the impulse formers and hence the control electrode pairs.

33. A sorter device according to claim 13 characterized in that a channel counter can be applied for the analysis of the particles as the particle sensor device, the magnitude of the sensor impulse being proportional to the particle volume.

34. A sorter device according to claim 33 characterized in that the channel counter is composed of a first counter electrode, a small orifice, and a second counter electrode, that the suspension flows through the orifice, that the first counter electrode and the second counter electrode are located at the upstream and downstream sides of the orifice, respectively, that the passage of a particle through the orifice corresponds to a change in the electrical resistance of the electrolytical system between the counter electrodes in accordance with the size of the particle, that the orifice is located in the electrolyte flow path between an entrance channel and the middle channel of the sorter device, and that the counter electrodes are located outside the flow path of the electrolyte and outside the device in relatively large containers.

35. A sorter device according to claim 33 characterized in that an entrance channel of the counter starts from a first container filled with pure electrolyte and containing a first counter electrode, that two side entrance channels join adjacent the downstream side of the orifice such that the suspension from the suspension capillary and the two side entrance channels enter laminarly into the middle channel of the sorter device, that the side entrance channels start from a second container filled with pure electrolyte and containing a second counter electrode and that the cross-section of the orifice is only a small fraction of that of the side entrance channels.

36. A sorter device according to claim 33 characterized in that a suspension capillary is located coaxially inside a counter entrance channel the downstream end of which has the form of a nozzle and is placed very closely to the upstream side of an orifice so that the suspension flows through the orifice in a very thin hydrodynamically focused stream, and that a first counter electrode is immersed in the particle free electrolyte filled first container where the upstream end of the counter entrance channel is also immersed.

37. A sorter device according to claim 30 characterized in that the control electrode pairs are operated in an electrically floating condition, and that the polarity of the counter voltage or current is chosen such that the coupling between the counter and the control electrodes is negative at the trailing edge of each control impulse, and that an electronic circuit prevents positive coupling between the counter and the sorter and reduces the noise level of the counter considerably.

38. A device for the reduction of the interparticle distance of particles suspended in electrolyte flowing in a channel of capillary dimensions, characterized in that from a suspension containing main channel of very small cross-section at least one side channel branches out substantially perpendicular to the main channel, that the side channels are provided with valve-electrode pairs, said valve electrode pairs being activated by an electronic system such that the amount of electrolyte between any two consecutive particles is reduced by some amount of electrolyte leaving the main channel via the side channels.

* * * * *

UNITED STATES PATENT AND TRADEMARK OFFICE
CERTIFICATE OF CORRECTION

PATENT NO. : 4,175,662  
DATED : November 27, 1979  
INVENTOR(S) : Tibor Zold

Page 1 of 2

It is certified that error appears in the above—identified patent and that said Letters Patent is hereby corrected as shown below:

| | | |
|---|---|---|
| Column 1, line 14 | : | Insert --protein-- before "content" |
| line 30 | : | "ultrasound" should be --ultrasonic-- |
| line 54 | : | "beeds" should be --beads-- |
| Column 3, line 54 | : | The comma"(,)" first occurrence should be a period --(.)-- |
| line 57 | : | "adjacing" should be --adjacent-- |
| Column 4, line 1 | : | Insert a hyphen (-) after "quies" |
| line 2 | : | "particle" should be --particles-- |
| line 4 | : | Insert a hyphen (-) after "lo" |
| line 5 | : | Insert a hyphen (-) after "chan" |
| Column 5, line 16 | : | Insert --which is capable of counting and sizing any kind of particles-- after "Mar. 22, 1978" |
| line 23 | : | "electronical" should be --electronic-- |
| line 59 | : | "or" should be --of-- |
| Column 10, line 11 | : | "electrolyts" should be --electrolyte-- |
| line 55 | : | "proteine" should be --protein-- |
| Column 11, line 22 | : | After "an" delete --the-- |
| line 23 | : | "are" should be --is-- |

UNITED STATES PATENT AND TRADEMARK OFFICE
CERTIFICATE OF CORRECTION

PATENT NO. : 4,175,662
DATED : November 27, 1979
INVENTOR(S) : Tibor Zold

It is certified that error appears in the above—identified patent and that said Letters Patent is hereby corrected as shown below:

Column 12, line 19 : After "circuit" delete --and-- line 41 : "particles" should be --particle--

Column 13, line 17 : "the" should be --a--

Signed and Sealed this

Fifteenth Day of July 1980

[SEAL]

Attest:

SIDNEY A. DIAMOND

Attesting Officer

Commissioner of Patents and Trademarks